United States Patent [19]

Reece et al.

[11] Patent Number: 5,691,158
[45] Date of Patent: Nov. 25, 1997

[54] SYSTEM AND METHOD FOR DETERMINING EFFICACY OF SUNSCREEN FORMULATIONS

[75] Inventors: Barry T. Reece, London, England; Michael G. Rozen, Irving, Tex.; David A. Deeds, Dallas, Tex.; Dale K. Roberts, Sanger, Tex.

[73] Assignee: Mary Kay Cosmetics, Inc., Dallas, Tex.

[21] Appl. No.: 137,822

[22] Filed: Oct. 15, 1993

(Under 37 CFR 1.47)

[51] Int. Cl.$^6$ .................................... G01N 33/53
[52] U.S. Cl. .................. 435/7.92; 250/493.1; 424/59; 424/60; 424/85.2; 422/50; 422/55; 422/82.05; 435/79; 435/4; 435/287.1; 435/287.2; 435/288.3; 435/288.4; 435/288.7; 436/501; 436/809; 436/815
[58] Field of Search .................. 422/50, 55, 82.05, 422/186.3; 250/504 R, 493.1; 435/7.9, 7.92, 4, 284, 287, 289, 290, 291, 287.1, 287.2, 288.7, 288.3, 288.4; 436/501, 63, 174, 807, 809, 815; 424/59, 60, 85.2

[56] References Cited

U.S. PATENT DOCUMENTS

| | | | |
|---|---|---|---|
| 4,025,795 | 5/1977 | Lackore et al. | 250/504 |
| 4,623,621 | 11/1986 | Pestka | 435/28 |
| 4,687,747 | 8/1987 | Lin | 436/527 |
| 4,923,697 | 5/1990 | Albeck et al. | 424/195.1 |
| 4,935,343 | 6/1990 | Allison et al. | 435/810 |
| 4,986,985 | 1/1991 | Grossman et al. | 514/934 |

OTHER PUBLICATIONS

Bell et al., "Use of Fabricated Living Tissue & Organ Equivalents . . . ", Pharmaceutical Applications of Cell and Tissue Culture to Drug Transport, 1991, vol. 218, pp. 51–65.
Nelson et al., "Effects of UV Irradiation in a Living Skin Equivalent", Photochemistry and Photobiology, 57(5), 1993 May 26, pp. 830–837.

"Sunscreen Product Testing Procedures for Determination of the Sun Protection Factor (SPF) Value and Related Labeling Claims", Federal Register vol. 43, No. 166, pp. 38259–38260, Aug. 25, 1987.

John C. Ansel, Thomas A. Luger and Ira Green, "The Effect of In Vitro and In Vivo UV Irradiation on the Production of ETAF Activity by Human and Murine Keratinocytes", The Journal of Investigative Dermatology, vol. 18, No. 6, pp. 519–523, 1983.

K. Punnonen, T. Puustinen, and C.T. Jansen, "UVB irradiation induces changes in the distribution and release of $^{14}C$-arachidonic acid in human keratinocytes in culture", Archives of Dermatological Research, V. 278, pp. 441–444, 1986.

Ronald D. Ley, Meyrick J. Peak, and Loretta L. Lyon, "Induction of Pyrimidine Dimers in Epidermal DNA of Hairless Mice by UVB: An Action Spectrum", The Journal of Investigative Dermatology, vol. 80, pp. 188–191, 1983.

Donald L. Bissett, Daniel P. Hannon and Thomas V. Orr, "An Animal Model of Solar–Aged Skin: Histological, Physical, and Visible Changes in UV–Irradiated Hairless Mouse Skin", Photochemistry and Photobiology, vol. 46, No. 3, pp. 367–378, 1987.

Thomas S. Kupper, "The Activated Keratinocyte: A Model for Inducible Cytokine Production by Non–Bone Marrow–Derived Cells in Cutaneous Inflammatory and Immune Responses" The Journal of Investigative Dermatology, V.94 pp. 146s–150s, 1990.

(List continued on next page.)

*Primary Examiner*—Christopher L. Chin
*Attorney, Agent, or Firm*—Akin, Gump, Strauss, Hauer & Feld, L.L.P.

[57] ABSTRACT

A system and method is disclosed employing a full thickness skin model for determining minimum sun protection factors (SPFs) of various sunscreen formulations by measuring the release of an inflammatory mediator in the skin model.

33 Claims, 5 Drawing Sheets

OTHER PUBLICATIONS

Yoshiki Miyachi, Sadao Imamura, and Yukie Niwa, "Decreased Skin Superoxide Dismutase Activity by a Single Exposure of Ultraviolet Radiation is Reduced by Liposomal Superoxide Dismutase Pretreatment", The Journal of Investigative Dermatology, vol. 89, pp. 111–112, 1987.

T. Schwarz, T.A. Luger, "Effect of UV Irradiation on Epidermal Cell Cytokine Production", Journal of Photochemistry and Photobiology, vol. 4, pp.1–13, 1989.

Boris M. Cumpelik, "Analytical Procedures and Evaluation of Sunscreens", Journal of the Society of Cosmetic Chemists, vol. 23, pp. 333–345, 1972.

Donald F. Robertson and Gordon A. Groves, "The Selection and Use of Topical Sunscreens", The Medical Journal of Australia, vol. 2, pp. 1445–1451, 1972.

Gordon A. Groves, Patricia Poh Agin, Robert M. Sayre, "In Vitro and in Vivo Methods to Define Sunscreen Protection", Australian Journal of Dermatology, vol. 20, p. 112, 1970.

Curtis A. Cole, Rory L. Van Fossen, "In Vitro Models for UVB and UVA Photo–protection", Sunscreens: Development, Evaluations, and Regulatory Aspects, N.J. Lowe and N.A. Shaath, editors, Marcel Dekker, N.Y., pp. 395–404, 1990.

A. Kobza Black, M.W. Greaves, C.N. Hensby, N.A. Plummer, "Increased Prostaglandins $E_2$ and $F_{2a}$ in Human Skin at 6 and 24 H After Ultraviolet B Irradiation (290–320 nm)", British Journal of Clinical Pharmacology, vol. 5, pp. 431–436, 1978.

Jurgen Fuchs, M.D., Ph.D., Margaret E. Huflejt, M.S., Laurie M. Rothfuss, A.B., David S. Wilson, A.B., Gerardo Carcamo, A.B., and Lester Packer, Ph.D., "Impairment of Enzymic and Nonenzymic Antioxidants in Skin by UVB Irradiation", Journal of Investigative Dermatology, vol. 93(6), Dec., 1993.

B. L. Diffey and J. Robson, "A New Substrate to Measure Sunscreen Protection Factors Throughout the Ultraviolet Spectrum," Journal of Society for Cosmetology Chemistry, vol. 40, pp.127–133, May/Jun. 1989.

Kevin D. Cooper, Patricia Fox, Gabrille Neises, and Stephen I. Katz, "Effects of Ultraviolet Radiation on Human Epidermal Cell Alloantigen Presentation: Initial Depression of Langerhans Cell–Dependent Function is Followed by the Appearance of $T6^-$ $Dr^+$ Cells That Enhance Epidermal Alloantigen Presentation", Journal of Immunology, vol. 134, No. 1, p. 129–137, Jan. 1985.

Thomas S. Kupper, Anne O. Chua, Patrick Flood, Joseph McGuire, and Ueli Gubler, "Interleukin 1 Gene Expression in Cultured Human Keratinocytes is Augmented by Ultraviolet Irradiation", Journal for Clinical Investigation, vol. 80, pp. 430–436, 1987.

Robert M. Sayre, Patricia Poh Agin, Deborah L. Desrochers, Edward Marlowe, "Sunscreen testing methods: In Vitro predictions of effectiveness", Journal of Society of Cosmetic Chemists, vol. 31, pp. 133–143, 1980.

INTERLEUKIN-I ALPHA RELEASE:
TIME VS. RELEASE

SYSTEM AND METHOD FOR DETERMINING EFFICACY OF SUNSCREEN FORMULATIONS

FIELD OF THE INVENTION

This invention generally relates to techniques for testing sunscreen formulations, and more particularly to an in vitro system and method employing artificial skin culture for testing the sun protection factor of sunscreen formulations.

BACKGROUND OF THE INVENTION

Exposure to ultraviolet (hereinafter referred to as "UV") radiation, especially radiation in the spectrum of 290–320 nm (hereinafter referred to as "UVB") and in the range of 320–410 nm (hereinafter referred to as "UVA"), has been shown to induce both physical and biochemical changes within the skin of living organisms. In an article by Ronald D. Ley, Meyrick J. Peak, and Loretta L. Lyon, entitled "Induction of Pyrimidine Dimers Epidermal DNA of Hairless Mice by UVB: An Action Spectrum", *The Journal of Investigative Dermatology*, Vol. 80, pages 188–191 (1983), it was shown that exposure to UV radiation induces pyrimidine dimer formation in DNA. In an article by Donald L. Bissett, Daniel P. Hannon, and Thomas V. Orr, entitled "An Animal Model Of Solar-Aged Skin: Histological, Physical, And Visible Changes In UV-Irradiated Hairless Mouse Skin", *Photochemistry and Photobiology*, Vol. 46, No. 3, pp. 367–378, (1987), the effect of UVB radiation on skin aging was demonstrated using a hairless mouse model. Moreover, it has been shown that exposure to UV radiation has been associated with increased prostaglandin synthesis, suppression of the immune response, and damage to the antioxidant defense mechanisms of the cell.

Chemical sunscreen formulations (i.e. formulations which absorb the UV radiation) or physical sunscreen formulations (i.e. formulations which reflect the UV radiation) protect the skin with topical application to the stratum corneum layer. As such, sunscreen formulations, typically in the form of lotions, represent an important category of consumer products, permitting the user to enjoy outdoor activities while reducing skin exposure to the harmful UVB and UVA radiation from the sun.

In the United States, sunscreen products are regulated as an over-the-counter drug. Accordingly, safety and sun protection factor (herein also referred to as "SPF") claims must be established in accordance with Food and Drug Administration regulations. The regulations require, inter alia, that the sun protection factor be determined under specific conditions using human subjects. A sun protection factor ("SPF") is a unitless number relative to the user's particular sensitivity to UV radiation. Specifically, if the user's skin exhibits reddening when exposed to the radiation of the sun having a particular intensity, over a known period of time, the application of a sunscreen having a SPF of "N" will extend that period of time by a factor of N. For example, if the user exhibits reddening when exposed to relatively constant radiation from the sun for ten minutes, the application of a SPF 4 product will typically allow the user to stay in the sun for up to forty minutes without skin redness.

Historically, prior to final human sun factor protection testing, in vivo screening studies were performed using laboratory animals such as guinea pigs or mice. The drawbacks to in vivo techniques include its time intensive nature, its non-repeatability, and that it usually requires the manufacturer of a product to use a contract laboratory to conduct the tests due to the complexity and the costs involved. Moreover, with the suspension or total ban of animal testing by many manufacturers of personal care products, a need exists for reliable in vitro testing.

Keratinocytes are the principal cells of the skin which respond to UV irradiation. The involvement of keratinocytes in UV-induced inflammatory reactions is discussed by John C. Ansel, Thomas A. Luger, and Ira Green, in their article entitled "The Effect of In Vitro and In Vivo UV Irradiation on the Production of ETAF Activity by Human and Murine Keratinocytes", *The Journal of Investigative Dermatology*, Vol. 81 pages 519–523 (1983). In their article, it was shown that there is an increase in interleukin-1α (herein also referred to as "IL-1α") production in keratinocytes when exposed to UV irradiation. In an article entitled "The Activated Keratinocyte: A Model for Inducible Cytokine Production by Non-Bone Marrow-Derived Cells in Cutaneous Inflammatory and Immune Responses", by Thomas S. Kupper, *The Journal of Investigative Dermatology*, Vol. 94, pages 146S–150S (1990), it was shown that keratinocytes which are grown in vitro do not produce IL-1α unless activated by a stimulus. Furthermore, in an article by K. Punnonen, T. Puustinen, and C. T. Jansén, entitled "UVB irradiation induces changes in the distribution and release of $^{14}C$-arachidonic acid in human keratinocytes in culture", *Archives of Dermatological Research*, Vol. 278 pages 441–444 (1986), it was shown that UVB irradiation induces a pathway of arachidonic acid ($C_{20}H_{32}O_2$) in the skin.

Accordingly, with the recent advancements and applications of cell and tissue culture assays as possible non-animal alternative safety and efficacy tests, there is a need for an in vitro system and method to provide a useful test for determining the efficacy and the value of sunscreen formulations.

SUMMARY OF THE INVENTION

To overcome the limitations in the prior art described above, and to overcome other limitations that will become apparent upon reading and understanding the present specification, the present invention discloses a system and a method for testing the efficacy and the sun protection factor of sunscreen formulations. The system and method employ artificial skin culture exposed to a controlled source of UV radiation such as a solar simulator, with a sunscreen formulation under test interposed therebetween. The artificial skin culture, in response to the UV radiation, releases an inflammatory mediator such as interleukin-1α which is detected by an assay and correlated to the efficacy of the sunscreen formulation. Multiple skin cultures may be exposed at constant intensity but for increasingly periods of predetermined time and assayed, to develop a time course study for determining a precise value for the sun protection factor. Thus, by blocking or partially blocking the skin cultures from the UV radiation with a sunscreen formulation under test, a minimum or precise value for the sun protection factor can be determined by assaying the artificial skin for the release of an inflammatory mediator.

A feature of the present invention is providing a rapid in vitro system and method for determining whether a prototype sunscreen formulation possesses a minimum desired sun protection factor.

Another feature of the present invention is screening for a minimum value or determining a precise value for the sun protection factor of a product without the use of animals or humans.

An advantage of the present invention is that sunscreen formulations which significantly lack their intended sun protection factor, can be identified and modifications or removal of such formulas can be made, prior to the pilot or final human sun protection factor testing.

Another advantage of the present invention is that with the use of a multiple port UV radiation source, determination of a precise sun protection factor can be readily made.

These and various other advantages and features of novelty which characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a specific example of a system and method in accordance with the present invention.

BRIEF DESCRIPTION OF THE DRAWINGS

Referring now to the drawings in which like reference numerals and letters indicate corresponding elements throughout the several views.

DETAILED DESCRIPTION OF THE PREFERRED EMBODIMENT

In the following description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention. It is to be understood that the drawings are not necessarily to scale and certain aspects depicted therein may be exaggerated to illustrate the invention more clearly.

Figure 1:
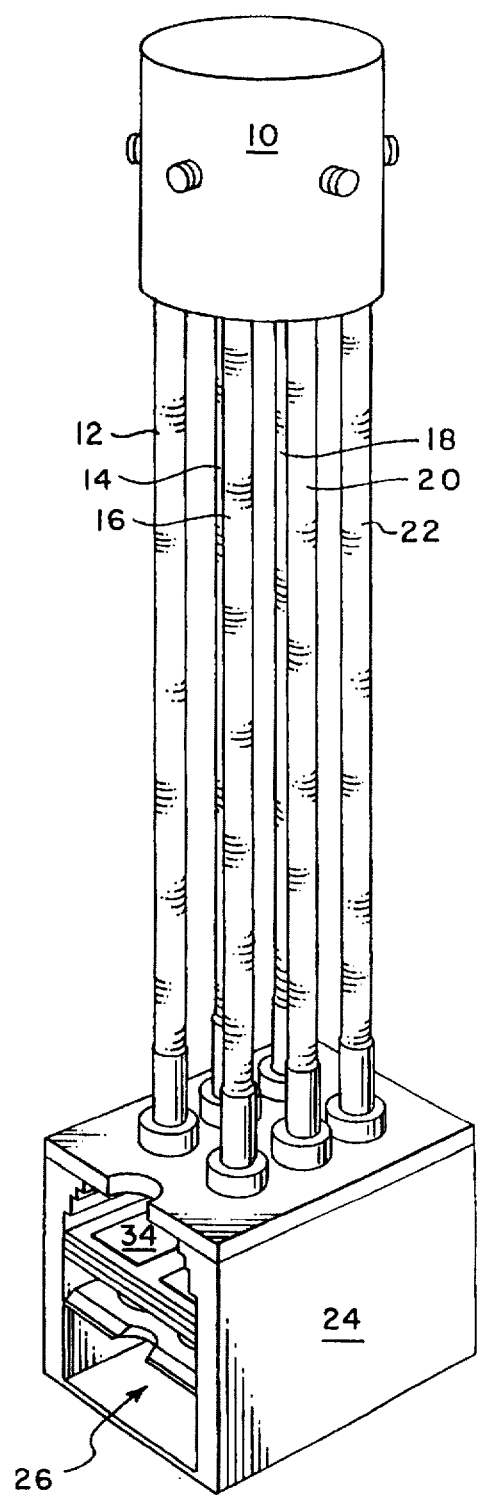
FIG. 1 is a general perspective view of a system in accordance with the present invention.
Figure 1A:
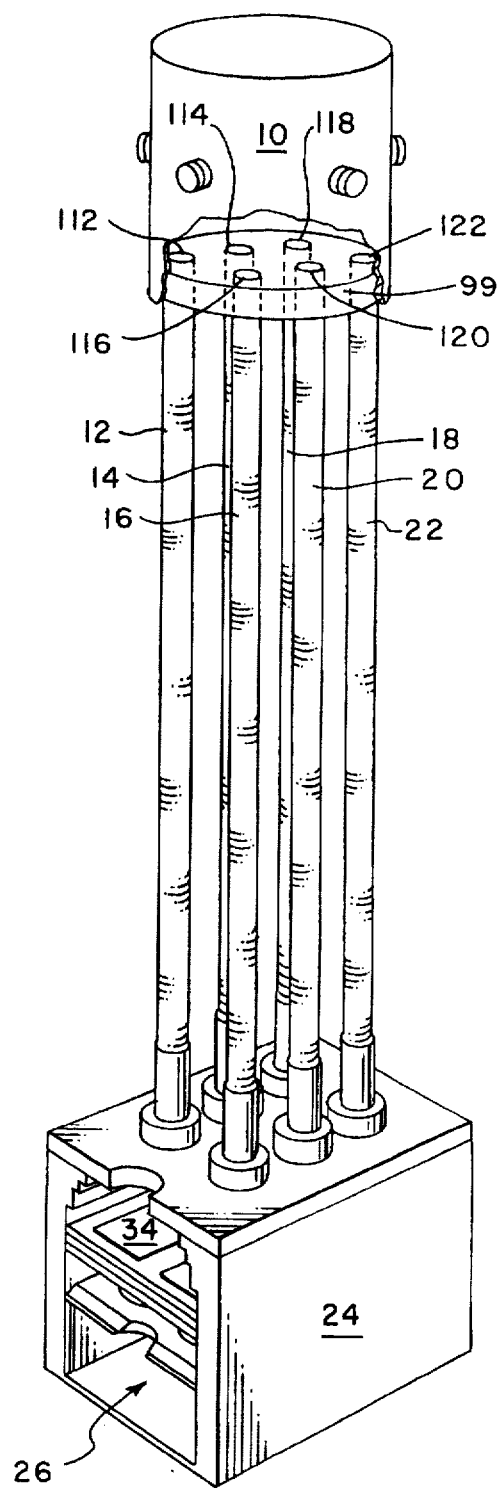
FIG. 1A is a perspective view of an alternate preferred embodiment of the system of FIG. 1.

Reference is made to FIG. 1 which depicts a general perspective view of a system in accordance with the principles of the present invention. A solar simulator 10 for generating UV radiation has six independently adjustable output ports coupled to a base unit 24 through six flexible fiber optic linkages 12, 14, 16, 18, 20, and 22 respectively. In a second preferred embodiment (FIG. 1A), the solar simulator 10 provides the UV radiation over a large unitary area with a template 99 having a plurality of independently adjustable shutters 112, 114, 116, 118, 120, and 122 interposed between the six linkages 12, 14, 16, 18, 20 and 22 and the solar simulator 10. The plurality of shutters in the second preferred embodiment are electronically controlled by a controller (not shown) for producing increasingly spaced exposure times, discussed in more detail hereinbelow. The shutters thus provide six independent UV radiation ports of substantially uniform intensity with six different exposure times. While various types of equipment would be acceptable for the simulator 10, one suitable type is that manufactured by the Solar Light Co. of Philadelphia, Pa. which includes a Xenon lamp for emitting UVA and UVB radiation at a preferred intensity of substantially 42 mJ/cm$^2$. Each of the six independently adjustable ports on the solar simulator 10 are set to emit substantially the same intensity of UV radiation (42 mJ/cm$^2$) but each are energized for increasingly spaced, predetermined durations. Thus, six overlapping but separate exposure periods are maintained for obtaining six skin cultures with varying exposure times. Specifically, all six ports are energized for a base period of time with port 1 being deenergized thereafter. Port 2 is then deenergized at a second benchmark time, port 3 is deenergized at a third benchmark time, port 4 is deenergized at a fourth benchmark time and so forth. By overlapping the exposure periods, the minimum testing time is limited only by the longest benchmark exposure time. By assaying the six skin cultures for inflammatory mediators such as Il-1α or eicosanoids and knowing the predetermined benchmark exposure periods for the ports, the sun protection factor (SPF) can be determined as discussed in detail hereinbelow. It should be readily apparent that other solar simulators with different number of ports can be used for collecting additional specimens without departing from the scope of the present invention.

Figure 2:
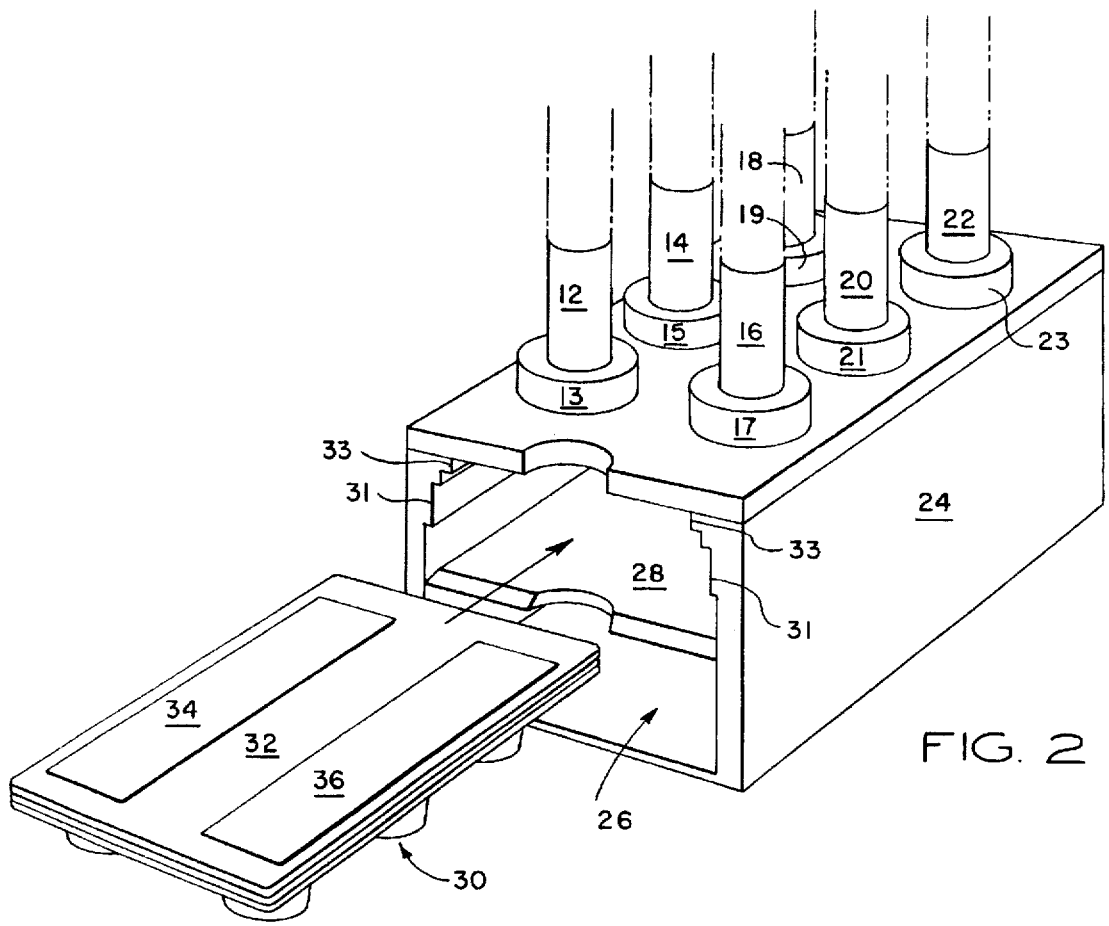
FIG. 2 is a detailed perspective view of the base portion of the system depicted in FIG. 1.
Figure 3:
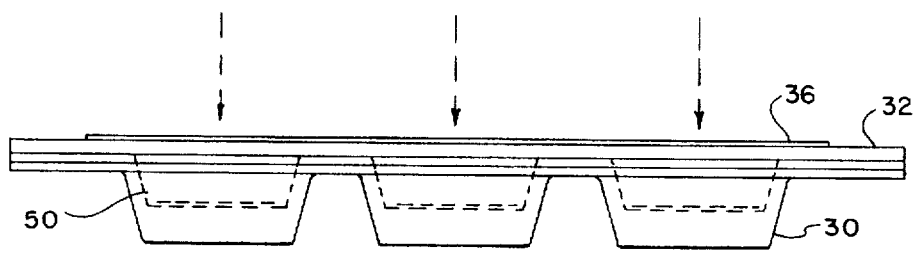
FIG. 3 is a side elevated view of the quartz plate, the substrate insert, and the culture tray depicted in FIG. 2.

Referring to FIG. 2, the base unit 24 includes six receptacle collars 13, 15, 17, 19, 21, 23 mounted in spaced relation on its top side for mating with the six fiber optic linkages 12, 14, 16, 18, 20 and 22 respectively. The base unit 24 further includes an opening 26 along one of its sides and a shelf 28 disposed approximately halfway in height therein and extending the length and the width of the base unit 24. A culture tray 30 forming a plurality of specimen wells is slidably disposed on top of the shelf 28 within the base unit 24 along notches 31 formed within its inner walls. As best seen in both FIGS. 2 and 3, covering the culture tray 30 is a flat quartz glass plate 32 having disposed thereon a first strip of specimen tape 34 and a second strip of specimen tape 36, preferably a low-density perforated polyethylene film, such as that sold under the trademark "TRANSPORE™" tape manufactured by the 3M Company of St. Paul, Minn. The quartz glass plate 32 is held in place on top of the culture tray 30 by notches 33 formed within the inner walls of the base unit 24. In the installed position within the base unit 24, the quartz glass plate 32 rests approximately 2 millimeters from the collars 13, 15, 17, 19, 21 and 23. With the culture tray 30 installed within the base unit 24, the specimen wells formed by the culture tray 30 are aligned under the collars 13, 15, 17, 19, 21 and 23 mounted on the top of the base unit 24 for direct exposure to UV radiation from the solar simulator 10. The first and second strips of specimen tape 34 and 36 are aligned above the wells formed by the culture tray 30 and below the collars 13, 15, 17, 19, 21 and 23 mounted on the top wall of the base unit 24. Each of the plurality of wells are exclusively exposed to one of the output ports from the solar simulator 10.

A sunscreen formulation under test, typically in the form of a lotion, is applied to the strips of specimen tape 34 and 36 at a preferable concentration of 2 mg/cm$^2$. The strips of specimen tape 34 and 36 simulate the irregular surface of the stratum corneum portion of the skin and allow for easy application of the sunscreen formulations under test. Moreover, the combination of the specimen tape 34 and 36 and the quartz glass plate 32 ensure that any inflammatory mediator released into the culture tray 30 is due to exposure of the skin cultures to the UV radiation and not to the interaction of the sunscreen formulation under test with the artificial skin cultures.

Figure 4:
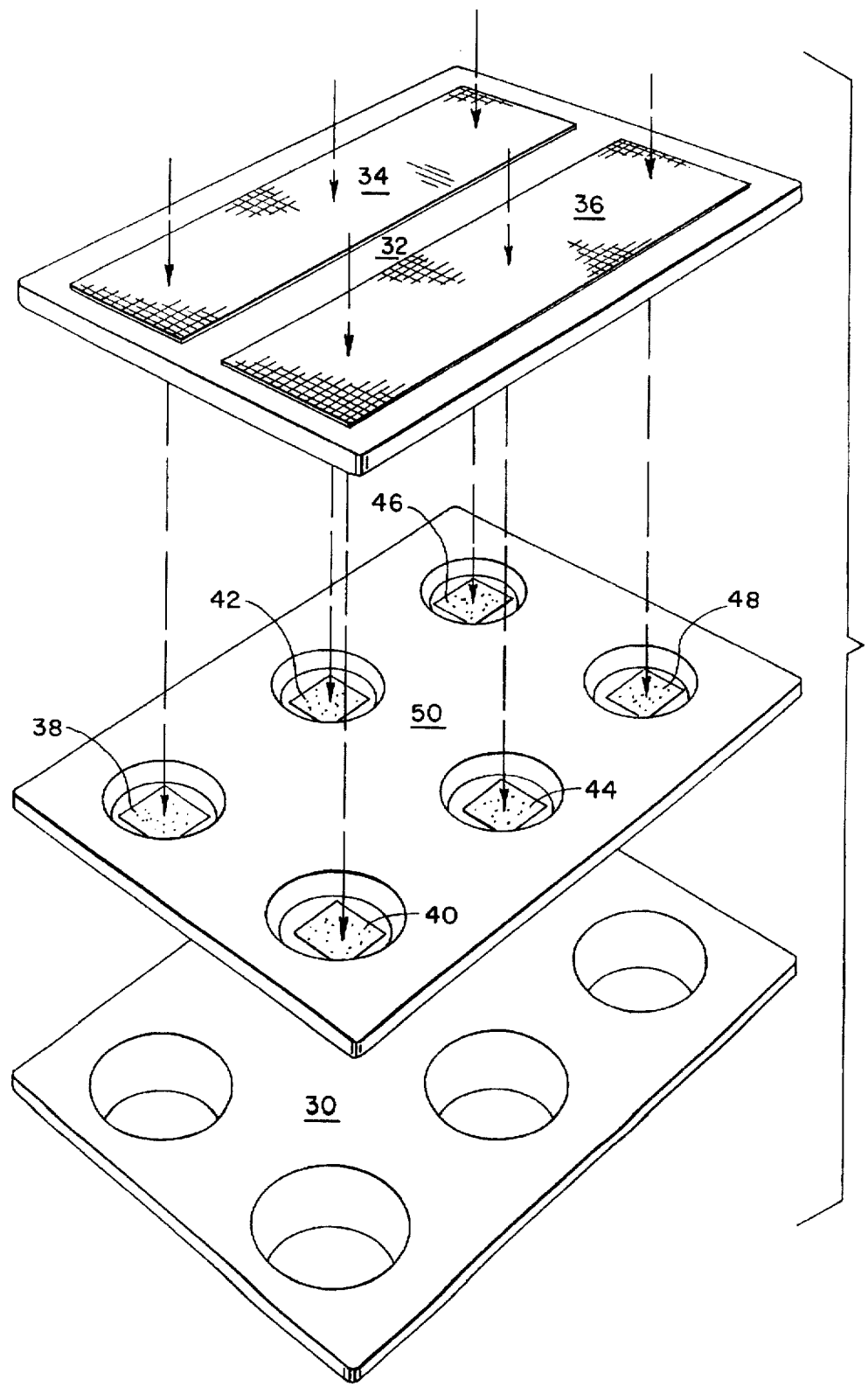
FIG. 4 is an exploded view of the assembly depicted in FIG. 3.

Referring now to FIG. 4, six artificial skin cultures 38, 40, 42, 44, 46, 48 comprising mitotically and metabolically active human dermal fibroblasts seeded onto a synthetic polyamide mesh such as nylon, and having a multilayered epidermis with a basal layer and a plurality of layers of differentiated and cornified keratinocytes, are disposed on a removable substrate 50 forming multiple wells corresponding to the wells formed by the culture tray 30. The removable substrate 50 provides for easy removal and disposal of the skin cultures 38, 40, 42, 44, 46, 48 after exposure, incubation, and assaying without disturbing the release of Il-1α. The removable substrate 50 in the preferred embodiment is a Millicell™ substrate insert manufactured by the Millipore Corporation of Bedford, Mass. Those skilled in the art will readily recognize other inserts for the substrate 50 without departing from the scope of the present invention.

The artificial skin cultures 38, 40, 42, 44, 46, 48 are cultivated from discarded human tissue and by way of illustration and not limitation, a particular embodiment for the artificial skin cultures 38–48 is a 3-dimensional tissue engineered human coculture such as that sold under the trademark "SKIN$^2$™" artificial skin culture from Advanced Tissue Sciences of La Jolla, Calif. Those skilled in the art will readily recognize other so-called artificial skin models for skin cultures 38, 40, 42, 44, 46, 48 without departing from the scope and the spirit of the present invention.

After being exposed to the UV radiation from the solar simulator 10, the substrate 50 including the artificial skin cultures 38–48 and the culture tray 30 are removed from the base unit 24 and incubated overnight in an incubator 60 having a tissue culture environment such as, but not limited to, a temperature of 37° C., a gaseous atmosphere of 5% $CO_2$ and 95% $O_2$, and at 100% humidity. Following incubation, the artificial skin cultures 38, 40, 42, 44, 46 and 48 are assayed for the presence of IL-1α with an enzyme immuneassay kit, such as available from R & D Systems of Minneapolis, Minn. The viability of the artificial skin cultures 38, 40, 42, 44, 46 and 48 is verified by the conversion of the dye 3[-4,5-dimethylthiazol-2-yl-]2,5,-diphenyltetrazolium bromide (commonly referred to as MTT) available from the Sigman Corporation of St. Louis, Mo.

Figure 5:
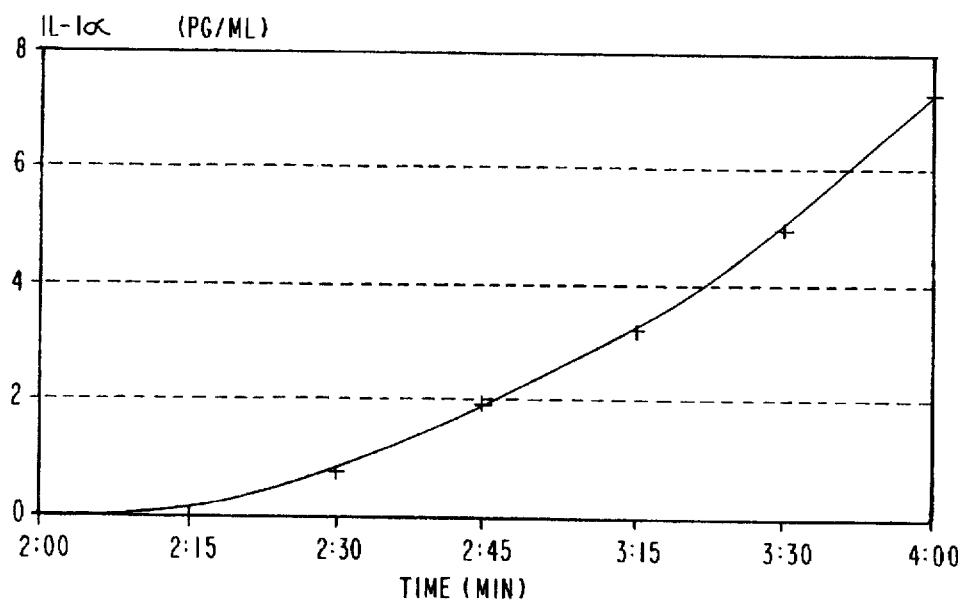
FIG. 5 is a graph of interleukin-1α release from an artificial skin culture versus exposure time to ultraviolet radiation, in accordance with the principles of the present invention.
Figure 6:
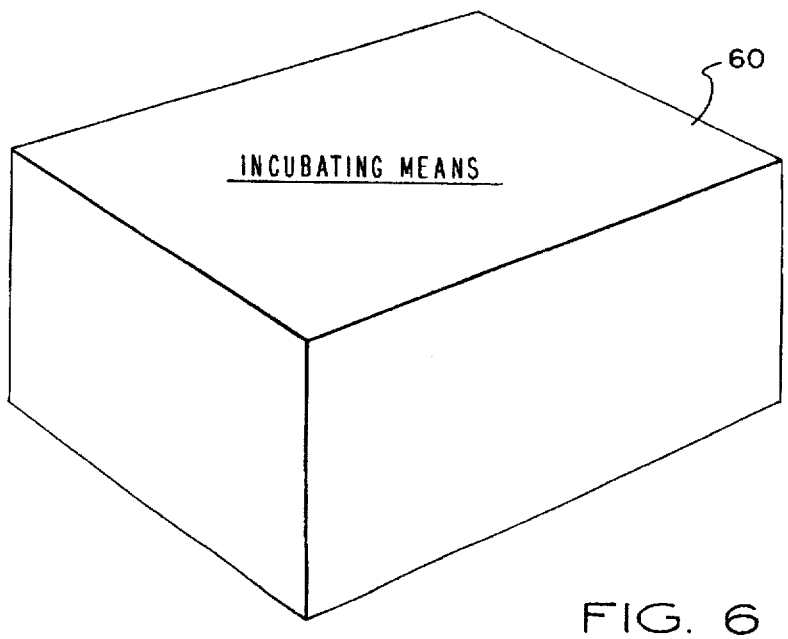
FIG. 6 is a general view of an incubating means used in the present invention.

As can be seen from FIG. 5, through experimentation, the Applicants have found a repeatable maximum unprotected exposure time of approximately two minutes for exposing the artificial skin cultures 38, 40, 42, 44, 46 and 48 to the UV radiation from the solar simulator 10 without the release of IL-1α. The minimum time is herein defined as the in vitro minimal erythema dose and is hereinafter referred to as "IVMED". IVMED is the in vitro dosage equivalent to the minimal in vivo erythema dose ("MED") for a human exposed to a fixed energy level of UV radiation which elicits a visually discernible erythemic response. Accordingly, the exposure time for determining the sun protection factor in vitro of a sunscreen formulation under test is scaled by IVMED. For example, a sunscreen formulation under test masking or partially masking a skin culture which releases IL-1α after eight minutes and not before, has a minimum sun protection factor of four.

Table I hereinbelow tabulates the Applicant's findings obtained from exposing the artificial skin to UV radiation with and without the application of sunscreen formulations to the strips of specimen tape 34 and 36. To ascertain if the IL-1α release is directly related to the ingredients of the sunscreen formulation, products with and without sunscreen formulations were tested. The findings tabulated in Table I verify that products without sunscreen active ingredients did not prevent the release of IL-1α while those products containing sunscreen active ingredients are successful in preventing its release.

TABLE I

Effects of Sunscreens on IL-1α Release

| Treatment | Exposure Times (min.) | Il-1α Release (pg/ml) |
|---|---|---|
| Sunscreen (SPF 4)* | 8 | 0 |
| No Sunscreen Control | | 6.50–7.81 |
| Sunscreen (SPF 8)* | 16 | 0 |
| No Sunscreen Control | | 28.60–34.83 |
| Sunscreen (SPF 12)* | 24 | 0 |
| No Sunscreen Control | | 33.71–34.37 |
| Sunscreen (SPF 15)** | 30 | 0 |
| Sunscreen (SPF 15)* | 30 | 0 |
| No Sunscreen Control | | 31.57–37.54 |

*chemical sunscreen
**physical sunscreen

The data in Table II hereinbelow illustrates a UV exposure time course study of the present invention with a sunscreen product having a known sun protection factor of 4. In this study, a product having a sun protection factor 4 was verified by utilizing three of the six ports on the solar simulator 10 and three skin cultures 38, 40, and 42. The cultures 38, 40, 42 were irradiated with UV radiation through the sunscreen product under test for progressive times predicted for a sun protection factor of 4 (8 minutes), a sun protection factor of 5 (10 minutes), and a sun protection factor of 8 (16 minutes), respectively. Additional specimens 44, 46, and 48 may be utilized as required, for testing sunscreen formulations having larger sun protection factors requiring longer exposure times for the release of IL-1α.

TABLE II

Time Course IL-α Release From Skin$^2$ Protected with Sunscreen

| Treatment | Exposure Times (min.) | IL-1α Release (pg/ml) |
|---|---|---|
| SPF 4 | 8 | 0 |
| SPF 4 | 10 | 5 |
| SPF 4 | 16 | 12.7 |

The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

We claim:

1. A system for testing efficacy of a sunscreen formulation comprising:

(a) means for generating ultraviolet radiation;

(b) means, coupled to the means for generating ultraviolet radiation, for containing at least one artificial skin culture;

(c) means, interposed between the means for generating ultraviolet radiation and the means for containing the at least one artificial skin culture, for holding a sunscreen formulation under test;

(d) means for incubating the at least one artificial skin culture after exposure to the means for generating ultraviolet radiation; and (e) means for assaying the at least one artificial skin culture for an inflammatory mediator.

2. A system for testing efficacy of a sunscreen formulation as recited in claim 1 wherein the means for generating ultraviolet radiation includes a plurality of ports for providing a plurality of ultraviolet radiation of substantially constant intensity for increasingly, predetermined spaced time intervals.

3. A system for testing efficacy of a sunscreen formulation as recited in claim 1 wherein the means for containing the at least one artificial skin culture further comprises a removable substrate for readily removing the at least one artificial skin culture.

4. A system for testing efficacy of a sunscreen formulation as recited in claim 1 wherein the means for incubating maintains a temperature of substantially 37° C.

5. A system for testing efficacy of a sunscreen formulation as recited in claim 1 wherein the means for incubating maintains a gaseous atmosphere of substantially 5% $CO_2$ and 95% $O_2$.

6. A system for testing efficacy of a sunscreen formulation as recited in claim 1 wherein the means for incubating maintains a condition of substantially 100% humidity.

7. A system for testing efficacy of a sunscreen formulation as recited in claim 1 wherein the means for assaying is an enzyme immunoassay kit.

8. A system for testing efficacy of a sunscreen formulation as recited in claim 1 wherein the inflammatory mediator is interleukin-1α.

9. A system for testing efficacy of a sunscreen formulation as recited in claim 1 wherein the inflammatory mediator is an eicosanoid.

10. A system for testing efficacy of a sunscreen formulation as recited in claim 1 further comprising a template interposed between the means for generating ultraviolet radiation and the means for containing the at least one artificial skin culture, the template including a plurality of independently controllable shutters.

11. A system for testing efficacy of a sunscreen formulation as recited in claim 1 further comprising means for testing viability of the at least one artificial skin culture.

12. A system for testing efficacy of a sunscreen formulation as recited in claim 11 wherein the means for testing viability is a 3(-4,5-dimethylthiazol-2-yl-)2,5,-diphenyltetrazolium bromide dye.

13. A method for testing efficacy of a sunscreen formulation comprising the steps of:

(a) generating ultraviolet radiation for passing through the sunscreen formulation;

(b) exposing at least one artificial skin culture to the ultraviolet radiation being passed through the sunscreen formulation under test, the sunscreen formulation being spaced from the artificial skin;

(c) incubating the at least one artificial skin culture at predetermined conditions;

(d) assaying the at least one artificial skin culture for an inflammatory mediator; and (e) correlating the inflammatory mediator assayed for to the efficacy of the sunscreen formulation.

14. A method for testing efficacy of a sunscreen formulation as recited in claim 13 wherein the sunscreen product under test is applied to a specimen tape which simulates a stratum corneum layer of skin.

15. A method for testing efficacy of a sunscreen formulation as recited in claim 13 wherein step (c) includes the steps of:

(i) maintaining a temperature of substantially 37° C.; and (ii) providing an atmosphere of substantially 5% $CO_2$, 95% at 100% humidity.

16. A method for testing the efficacy of a sunscreen formulation as recited in claim 13 further comprising the step of verifying viability of the at least one artificial skin culture after the said incubating.

17. A method for testing efficacy of a sunscreen formulation as recited in claim 16 wherein the step of verifying viability is conversion of a 3(-4,5-dimethylthiazol-2-yl-)2,5,-diphenyltetra-zolium bromide dye.

18. A method for testing efficacy of a sunscreen formulation as recited in claim 13 wherein the step of generating ultraviolet radiation comprises the steps of generating ultraviolet radiation of substantially uniform intensity from a plurality of ports at increasing predetermined time intervals.

19. A method for testing efficacy of a sunscreen formulation as recited in claim 18 further comprising the step of identifying which of the at least one artificial skin culture released an inflammatory mediator.

20. An in vitro method for determining efficacy of a sunscreen formulation comprising the steps of:

(a) placing at least one artificial skin culture into a culture tray;

(b) affixing at least one strip of specimen tape to a glass plate;

(c) applying a sunscreen formulation to at least one strip of specimen tape;

(d) covering the culture tray with the glass plate;

(e) exposing at least one artificial skin culture to ultraviolet radiation being passed through the sunscreen formulation;

(f) incubating at least one artificial skin culture for a predetermined period of time, at a predetermined temperature, in a predetermined atmosphere;

(g) assaying at least one artificial skin culture for an inflammatory mediator; and (h) correlating the inflammatory mediator assayed for to the efficacy of the sunscreen formulation.

21. A method for determining efficacy of a sunscreen formulation as recited in claim 20 wherein step (a) further includes the step of placing a specimen insert in between the at least one artificial skin culture and the culture tray.

22. A method for determining efficacy of a sunscreen formulation as recited in claim 20 wherein the predetermined temperature and the predetermined atmosphere in step (f) is substantially 37° C. and 5% $CO_2$ and 95% $O_2$ respectively.

23. An in vitro method of determining a sun protection factor for a sunscreen formulation comprising the steps of:

exposing a plurality of artificial skin cultures through a sunscreen formulation under test, the sunscreen formulation being spaced from the artificial skin cultures, to ultraviolet radiation of substantially constant intensity, the plurality of artificial skin cultures being exposed for overlapping but separate increasingly spaced predetermined periods of time;

assaying the plurality of artificial skin cultures for presence of an inflammatory mediator;

identifying an artificial skin culture which releases the inflammatory mediator and its corresponding exposure time to ultraviolet radiation; and scaling the corresponding exposure time by a predetermined constant to obtain a sun protection factor.

24. A system for testing the efficacy of a sunscreen formulation comprising:

(a) first means for generating ultraviolet radiation;

(b) second means disposing at least one artificial skin culture in the path of said ultraviolet radiation; and (c) third means holding said sunscreen formulation under test interposed between said first ultraviolet radiation generating means and said second artificial skin culture disposing means, and being spaced from said artificial skin culture within said path.

25. A system for testing efficacy of a sunscreen formulation as recited in claim 24 wherein said third means is a light transmissive means.

26. A system for testing efficacy of a sunscreen formulation as recited in claim 25 wherein said light transmissive means for holding said sunscreen formulation has an irregular surface.

27. A system for testing efficacy of a sunscreen formulation as recited in claim 26 wherein said light transmissive means comprises one or a combination of glass, quartz glass or specimen tape.

28. A system for testing efficacy of a sunscreen formulation as recited in claim 25 further comprising a template interposed between said first means for generating ultraviolet radiation and said second means disposing at least one artificial skin culture in the path of said ultraviolet radiation, said template including a plurality of independently controllable shutters.

29. A method for testing efficacy of a sunscreen formulation comprising:

(a) generating ultraviolet radiation for passing through said sunscreen formulation;

(b) exposing, for a period of time, at least one artificial skin culture to said ultraviolet radiation being passed through said sunscreen formulation under test, the sunscreen formulation being disposed on a surface other than said artificial skin, said surface being disposed such that said ultraviolet radiation to which said artificial skin is exposed passes through said sunscreen formulation;

(c) assaying said at least one artificial skin culture for an inflammatory mediator; and (d) correlating said inflammatory mediator assayed for to said period of time for which said at least one artificial skin culture was exposed to said ultraviolet radiation to determine the efficacy of said sunscreen formulation.

30. A method for testing efficacy of a sunscreen formulation as recited in claim 29 further comprising incubating said at least one artificial skin culture at predetermined conditions.

31. A method for testing efficacy of a sunscreen formulation as recited in claim 30 wherein said at least one artificial skin culture is incubated at substantially 37° C.

32. A method for testing efficacy of a sunscreen formulation as recited in claim 30 wherein said at least one artificial skin culture is incubated in a gaseous atmosphere of substantially 5% $CO_2$ and 95% $O_2$.

33. A method for testing efficacy of a sunscreen formulation as recited in claim 30 wherein said at least one artificial skin culture is incubated in an atmosphere of substantially 100% humidity.

* * * * *